United States Patent [19]

Thompson

[11] Patent Number: 5,096,668
[45] Date of Patent: Mar. 17, 1992

[54] DIAGNOSTIC TEST SLIDE

[75] Inventor: Thomas E. Thompson, Saline, Mich.

[73] Assignee: Difco Laboratories, Detroit, Mich.

[21] Appl. No.: 515,043

[22] Filed: Apr. 26, 1990

[51] Int. Cl.$^5$ .............................................. G01N 33/48
[52] U.S. Cl. ........................................ 422/58; 422/57; 435/805; 436/166
[58] Field of Search ................ 422/57, 58; 436/166, 436/169; 435/12, 18, 24, 25, 299, 301, 805, 810

[56] References Cited

U.S. PATENT DOCUMENTS

| | | | |
|---|---|---|---|
| 3,416,998 | 12/1968 | Steitfeld | 435/805 X |
| 4,225,557 | 9/1980 | Hartl et al. | 422/58 X |
| 4,234,683 | 11/1980 | McMillan | 435/18 |
| 4,353,824 | 10/1982 | Schindler et al. | 435/18 X |
| 4,472,353 | 9/1984 | Moore | 422/58 |
| 4,565,783 | 1/1986 | Hansen et al. | 435/805 X |
| 4,603,108 | 7/1986 | Bascomb | 435/24 X |
| 4,767,702 | 8/1988 | Cohenford | 435/810 X |
| 4,824,640 | 4/1989 | Hildenbrand et al. | 422/57 X |

Primary Examiner—Robert J. Warden
Assistant Examiner—Stephanie Blythe
Attorney, Agent, or Firm—Barnes, Kisselle, Raisch, Choate, Whittemore & Hulbert

[57] ABSTRACT

A diagnostic test slide for performing diagnostic tests for detecting the presence of microogranisms, enzymes or metabolites comprising a plastic film having a coating therein comprising a carrier and a reagent. The coated film is placed in a mount that is constructed and arranged to form a border around a portion of the film. A method is provided for making the test slide utilizing conventional, automated devices for making coated photographic films, and conventional, automated devices for mounting slide film in mounts.

42 Claims, 1 Drawing Sheet

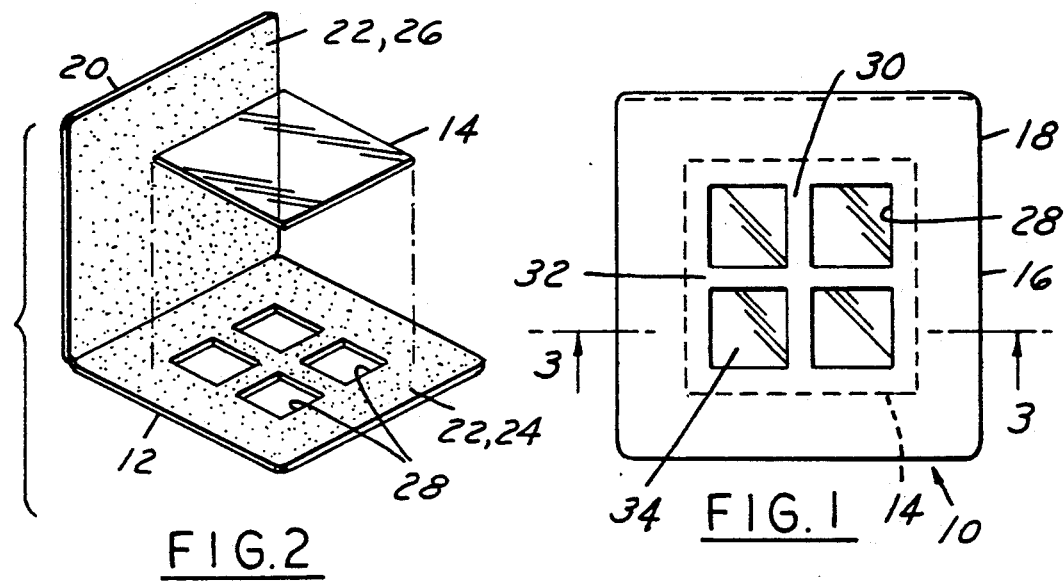
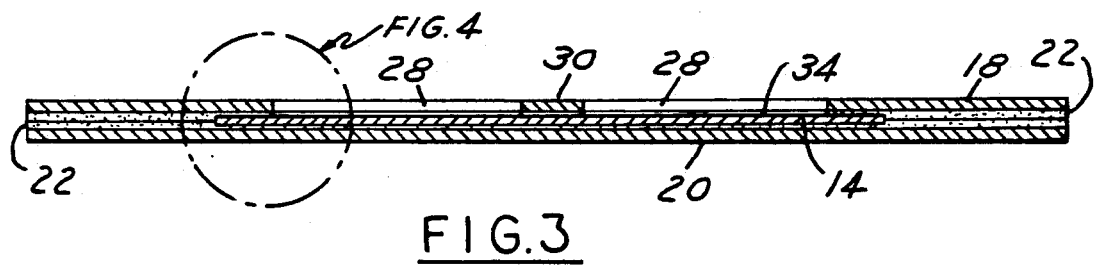
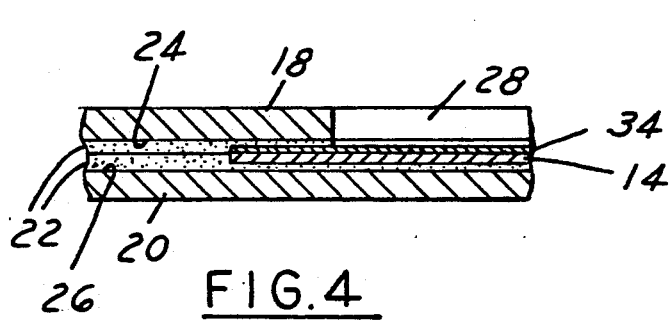

DIAGNOSTIC TEST SLIDE

FIELD OF THE INVENTION

This invention relates to a test slide for performing diagnostic tests.

BACKGROUND AND SUMMARY OF THE INVENTION

Planar slides and cards are used to perform diagnostic tests, including blood, urine and sputum chemistry tests as well as blood typing. Similar layered devices containing immobile nutrient components are used for culturing microorganisms. The cards and slides commonly contain a protective cover to protect and preserve the specimen or culture media during incubation or for storage purposes.

U.S. Pat. No. 3,990,850 describes a test card, which includes a substrate that has a test surface which is substantially insoluble in, impermeable to, non-absorbent to and wettable by water and carrying a dried test reagent. An er'd flap folds over the test area to enclose and preserve the specimen in a blood typing test. The card has a spot of blood typing anti-serum to which the blood sample is added. The flap has bonded thereon an absorbent blotting paper around the test area. The results may be viewed through a transparent plastic opening or window in the now folded flap.

U.S. Pat. No. 3,996,006 shows a test sheet which includes a sheet underlying openings in the front panel. Reagents are added to the paper sheet. The sheet may be divided into test sections. The '850 and '006 test slides are described as useful for immunological tests.

The manufacture of these devices, if mentioned, is by spotting the test reagents in the reaction area and drying the test card. During manufacture, each card would be handled individually. For example, U.S. Pat. No. 4,668,472 generally describes manufacturing by forming cups or wells into which the reagents are dispensed. The forming, filling and drying operations can be performed on the same machine, with wells of the reagent prepared and cut out for assembly. Although this may streamline the manufacture, it limits the flexibility of manufacturing and leads to variability, that is, nonuniform reaction surface preparation.

U.S Pat. No. 4,565,783 describes a device for culturing and observing microorganisms which may also be used for microbiological tests using antibiotics. A substrate is coated with an adhesive and a water soluble powder, which includes a nutrient or gel, which is adhered to the adhesive. A coversheet protects the culture and microorganism from contamination during incubation and growth. The device also includes an opening with limits for retaining fluid. This device is useful where incubation is required and where liquids are added. The device requires a cover sheet to isolate the contents from the environment, prevent evaporation and to prevent contact by the user during incubation and handling. Thus the prior art has provided test cards and slides for culturing microorganisms and for wet specimen analysis.

An objective of the present invention is to provide a test slide for performing simple microbiology diagnostic tests; which is in a new and useful format; which is constructed so as to not require assembly after the analysis is initiated; which has a test reagent carried on the slide in a dry format, ready for use; wherein the test reagent is conveniently included in a dry carrier without the need for adhesive; which can be readily handled; and which is also more economical and easier to manufacture than prior art slides and cards.

It is also an objective of the invention to provide for a process that allows automated or semi-automated assembly of the test slides which is labor saving, which is economical, and which eliminates variability of reactions by preparing the reaction surface in a uniform manner.

In accordance with the invention, the test slide comprises a plastic substrate strip or chip, which is transparent and dimensionally stable, and has a diagnostic reagent coating on an area thereon, and a mount constructed and arranged to form a border around and behind the substrate chip. The mount has rigid back and front walls or sides with inner surfaces which have a layer of self-adhesive adhesive and the substrate strip is positioned between the walls of said mount. The adhesive layers are !bound to one another by the adhesive to secure the substrate in the mount and to keep the mount assembled. The mount has at least one opening in the front wall overlying the diagnostic reagent area on the strip, providing access to a coating on the strip which includes a diagnostic reagent. The back wall is opaque to provide contrast for the transparent substrate.

BRIEF DESCRIPTION OF THE DRAWINGS

FIG. 1 is a top view of the test slide embodying the invention.

FIG. 2 is an exploded view of the elements of the slide of FIG. 1, prior to assembly.

FIG. 3 is a sectional view taken along line 3—3 of FIG. 1.

FIG. 4 is an enlarged sectional view taken at the encircled portion of FIG. 3.

DETAILED DESCRIPTION OF THE PREFERRED EMBODIMENT

Referring to FIGS. 1 and 2, there is shown a test slide 10 which embodies the invention. The slide 10 basically comprises a mount 12 and a plastic substrate strip 14. The mount 12 is constructed and arranged to form a border 16 around the strip of film 14. The strip 14 is stabilized and secured by the mount 12. The mount 12 has a rigid front wall 18 and a rigid rear wall 20. Preferably, the mount 12 is of a plastic or cardboard material.

As shown in FIGS. 1, 3 and 4, a pressure sensitive adhesive 22 is coated on the interior surfaces 24, 26 of the front wall 18 and rear wall 20, respectively.

The front wall 18 has at least one opening 28 to provide access to the strip 14. Preferably, there are four spaced openings 28, formed in the wall 18 by cross pieces 30, 32 of the wall 18.

As shown in FIG. 4, a coating 34 is bonded to the surface of strip 14 which is applied to the strip 14 before it is enclosed by the mount 12. The coating 34 comprises a diagnostic reagent. The coating 34 has a high melting point, and is dry and stable. Desirably, the coating remains stable and sticky when wetted. The coating may include gelatin, polygalacturonic acid, pectin, agar, agarose, cellulose, carboxymethyl cellulose, guar, xanthan, acacia, and similar plant gums, starch, polyacrylamide, polyvinyl alcohol, polyvinyl chloride.

The rear wall 20 is opaque in the area exposed by each opening 28, so as to provide contrast to the strip of film 14 which is transparent. Desirably, the strip of film 14 is less than 1/64 or 0.015 of an inch thick and is preferably 0.005 of an inch thick. The coating 34 desirably has a coating weight of less than 2 mg (milligrams) per square inch and preferably 1 mg per square inch.

Preferably, the strip 14 is made of plastic material selected from the group of polyethylene, polyester, PVC (poly vinyl chloride), PET (polyethylene terephthalate), PETG (polyethylene terephthalate glycol modified) and cellulose triacetate.

Advantageously, the test slide 10 may be manufactured in a relatively economical continuous processes. The strip 14 is of a plastic which is flexible and dimensionally stable. Therefore, the strip 14 can be handled as roll stock. The coating 34 can be applied to large rolls of plastic and cut down to final size lowering coating costs. The strip 14, once coated, can also be rolled and handled as roll stock. The strip 14 and mount 12 can be handled by commercially available, inexpensive, photographic slide mounting machines, allowing automated assembly of the slide 10. Commercial machines can also print alpha-numerical data onto the mount 12, lowering production costs further. Finally, the strip 14 can be coated by conventional coating equipment. Importantly, existing standard technology for the coating industry and the film making industry can be utilized.

Strips can be formed from sheet or roll stock of plastic. The coating may be applied to the sheet or roll stock and after it has dried, the strips may be formed by cutting the coated sheet or roll stock to the desired size. It has been found that sheet or roll stock is available, having a width in the range of 2" to 48" and we have produced coated strips from the stock which are approximately 35 mm wide. The stock may be cut using rotary knives in an automated process.

The strips of the invention are not required to be perforated whereas conventional 35 mm photographic film is often perforated. Therefore, it may be necessary to modify the conventional slide mounting device to adapt to roll stock, which is not perforated. For example, the sprockets on the rollers or wheels of a conventional slide mounting device may need to be replaced.

Advantageously, conventional film coating devices can be used to coat roll stock. For example, devices for coating an emulsion onto a photographic film, are well known and available. The conventional film coating devices are automated devices which coat, dry and roll up the coated film in a continuous process. The coating may be applied by means of extrusion, dipping or spraying. The coating may also be applied using a wire wound draw down bar where the wire diameter is in the range of about 0.006 to 0.018 inches in diameter.

The slide 10 facilitates the performing of diagnostic tests including, but not limited to, cytochrome c oxidase, beta lactamase and L-alanine amino peptidase (a Gram stain replacement test). In the cytochrome c oxidase test, a positive reaction may be indicated by a color change of organic electron acceptors or donors. In this test, the diagnostic reagent may incorporate ascorbic acid and tetramethyl phenylene diamine dihydrochloride.

In the beta lactamase test, the active part of a beta lactam antibiotic is a beta lactam ring which has a defined chemical composition. Organisms which possess beta-lactamases, may be resistant to the antibiotic by breaking open the ring. The beta lactamase test is a test for the presence of enzymes that cleave the beta lactam ring. For example, Penicillin G and chromogenic cephalosporins may be used as the active component of the reagent layer.

The L-alanine amino peptidase test is a test which correlates well with the well known Gram stain technique in microbiology. If the chromogenic substrate is cleaved, the organism is a Gram negative strain. If the substrate is not cleaved, the organism is a Gram positive strain.

Examples of additional tests that can be performed in this format include: Phosphatase using indoxyl or bromo-chloro-indoxyl phosphate, glucuronidase, urease, ortho-nitrophenyl galactosidase, acid from sugar fermentation, pyrrolidoxyl aminopeptidase, esterase, N-acetyl-B,D-galactosamidase, protease and hydrogen sulfide production are examples of assays that can be performed in this format. Fluorogenic substrates can be incorporated into the film as the bioactive reagent. 4-Methylumbelliferyl glucuronide is an example. Organisms that produce glucuronidase, such as Escherichia coli, will cleave the reagent, producing methylumbelliferone. This reaction can be monitored by shining a ultraviolet lamp on the film. A blue fluorescence will indicate a positive reaction. No fluorescence will be indicative of a negative reaction.

The presence of any microbial enzyme of interest in diagnostics can be monitored using this format, providing either the creation or the cleavage of a chromogen or fluorogen occurs.

EXAMPLE 1

METHOD OF MAKING A CYTOCHROME C OXIDASE TEST SLIDE (1) A cellulose triacetate film of 5 thousandths of an inch thickness was used.

(2) A gelatin/reagent mixture was prepared which included:
 (a) Bacto ® gelatin (Difco Laboratories, Detroit, MI) 12% wt/volume 10 mls
 (b) Ascorbic acid solution 0.1% 1.1 mls
 (c) NNN'N' tetramethyl-1, 4-phenylene diamine dihydrochloride 0.1 g in distilled or deionized water.

(3) The gelatin solution was melted, cooled to approximately 35° C., and the reactive components were added.

(4) The gelatin/reagent mixture was applied to the film at about 35° C. using a #12 draw down bar yielding a coating weight of approximately 1 mg/ sq. inch (dry).

(5) The coated film was dried in air overnight.

(6) The film was cut into pieces approximately 35 mm by 37 mm.

(7) The film was mounted in plastic or paper slide mounts.

EXAMPLE 2

Method of making a Beta-lactamase test slide (1) A cellulose triacetate film of 5 thousandths of an inch thickness was used.

(2) A gelatin/reagent mixture was prepared which included:
 (a) Bacto ® gelatin 12% wt/volume
 (b) Chlorophenol red solution 0.5% 2.5 mls/5 mls
 (c) Sodium phosphate buffer 1 mM 5 mls
 (d) Penicillin G. potassium salt 15 grams (3) The gelatin/reagent mixture was adjusted to pH 8.5 with 1N sodium hydroxide and applied to the film at about 35° C. yielding a coating weight of approximately 1 mg/sq. inch (dry).

(4) The coated film was dried in air overnight.

(5) The film was cut into pieces approximately 35 mm by 37 mm.

(6) The film was mounted in plastic or paper slide mounts.

EXAMPLE 3

METHOD OF MAKING A L-ALANINE AMINO PEPTIDASE TEST SLIDE (1) A cellulose triacetate film about 5 thousandths of an inch thickness was used.

(2) A gelatin/reagent mixture was prepared which included:

(a) Bacto ® gelatin 12% wt/volume, 10 mls.

(b) L-alanine nitro anilide, at approximately 0.5% in the gelatin solution.

(3) The gelatin/reagent mixture was applied to the film at about 35° C. yielding a coating weight of approximately 1 mg/sq. inch (dry).

(4) The coated film was dried in air overnight.

(5) The film was cut into pieces approximately 35 mm by 37 mm.

(6) The film was mounted in plastic or paper slide mounts.

There are other reagents which may be used to make the test slide. For the oxidase test the reagents include other reducing agents, such as thioglycollate, sodium sulfide, mercaptoethanol, dithiothreitol, dithioerythritol and other oxidase substrates, such as p-aminodiethylaniline oxalate.

For the beta-lactamase test the reagents may include other antibiotics, such as penicillin V, nitrocefin and related compounds (Glaxo), cephalothin and other cephalosporins, PADAC (Pyridinum 2-AZO-p-dimethylaniline chromophore (Hoechst-Roussell)) and chromogenic cephalosporins as cited in U.S. Pat. Nos. 4,525,156 and 4,353,824 and the like. Other buffers include citrate, Hepes, tris, maleate, barbitone, and the like. Other pH indicators include phenol red, brom thymol blue, brom cresol purple and the like.

EXAMPLE 4

METHOD OF PREPARING OXIDASE AND GRAM DIAGNOSTIC TESTS

The user rubbed 1 to 4 colonies of microorganisms onto the reagent on the slide through an aperture. The Oxidase positive organism such as *Pseudomonas aeruginosa* rehydrated and metabolized the substrates resulting in a reaction that produced a color change to purple or dark purple within 30 seconds. An organism negative for the test, such as *Escherichia coli*, will be unable to oxidize the substrate and no color change will result. The user read the positive or negative result through the aperture of the test card.

EXAMPLE 5

METHOD OF PERFORMING BETA-LACTAMASE TEST

The user rehydrated the reagent with 15 microliters (one drop) of water and suspended 1-2 colonies of microorganisms in the drop, or suspended the colonies in a small amount of water and added one drop of the suspension to the reagent on the slide. A color change resulted, based on the cleavage of the beta-lactam ring and net acidification of the reagent mixture or of the formation of a chromogen, in the case of the chromogenic cephalosporin substrates for beta-lactamese positive strains, such as Haemophilus influenzae ATCC 35056. Beta-lactamase negative strains, such as Haemophilus influenzae ATCC 8149 developed no color change and the drop remained pink within the 60 minute test duration.

It can thus be seen that in these tests, microbial biomasses from colonies or metabolites are added onto a slide coated with a reagent. A color change indicates that enzymes produced by the microorganisms have altered the reagent. The tests are conveniently done with the diagnostic slide which does not require assembly after the analysis is done; which has a test reagent on the slide; and which is easy to handle.

Obviously, many modifications and variations of the present invention are possible in light of the above teachings. Other microbiological tests which may be performed include: indole, catalase, coagulase, urease, $H_2S$, Voges-Proskauer, bile esculin, phosphatase, B-glucosidase, and citrate utilization. Therefore, within the scope of the appended claims, the present invention may be practiced otherwise than as specifically described.

I claim:

1. A test slide for performing diagnostic tests for detecting the presence of microorganisms, their enzymes and metabolites, said test slide comprising a plastic film having a top surface and a bottom surface, said plastic film being dimensionally stable and impervious to liquids, a coating bonded by its own properties to the top surface of said film, said coating comprising a carrier and a diagnostic reagent, said coating having a high melting point, being dry and stable, and water soluble, said reagent being capable of rehydration at room temperature by application of a microorganism, enzyme or metabolite to the coating (with or without the addition of water) to the coating such that it changes spectroscopic properties upon exposure to a specific microorganism, enzyme or metabolite, a mount comprising a rear wall and a front wall, said front wall having an opening therein, said coated film being mounted between said rear wall and said front wall such that said opening in said front wall overlies said top surface of said film exposing a portion of the coating through said opening.

2. The test slide set forth in claim 1 wherein said coating is bonded to the entire top surface of said film.

3. The test slide set forth in claim 1 wherein said plastic film is selected from the group consisting of polyethylene, PVC (polyvinyl chloride), PET (polyethylene terephthalate), PETG (polyethylene terephthalate glycol modified), polyester, and cellulose triacetate.

4. The test slide set forth in claim 1 wherein said carrier in said coating is selected from the group consisting of gelatin, polygalacturonic acid, pectin, agar, agarose, cellulose, carboxymethyl cellulose, guar, xanthan, acacia, plant gums, starch, polyvinyl alcohol, polyvinyl chloride and polyacrylamide.

5. The test slide set forth in claim 1 wherein said diagnostic reagent comprises a reagent for detecting oxidase.

6. The test slide set forth in claim 1 wherein said diagnostic reagent comprises a reagent for detecting beta lactamase.

7. The test slide set forth inn claim 1 wherein said diagnostic reagent comprises a reagent for detecting L-aniline amino peptidase.

8. The test slide set forth inn claim 1 wherein said diagnostic reagent comprises a reagent for detecting indole.

9. The test slide set forth in claim 1 wherein said diagnostic reagent comprises a reagent for detecting catalase.

10. The test slide set forth in claim 1 wherein said diagnostic reagent comprises a reagent for detecting coagulase.

11. The test slide set forth in claim 1 wherein said diagnostic reagent comprises a reagent for detecting urease.

12. The test slide set forth in claim 1 wherein said diagnostic reagent comprises a reagent for detecting $H_2S$.

13. The test slide set forth in claim 1 wherein said diagnostic reagent comprises a reagent for detecting Voges-Proskauer.

14. The test slide set forth in claim 1 wherein said diagnostic reagent comprises a reagent for detecting bile esculin.

15. The test slide set forth in claim 1 wherein said diagnostic reagent comprises a reagent for detecting phosphatase.

16. The test slide set forth in claim 1 wherein said diagnostic reagent comprises a reagent for detecting B-glucosidase.

17. The test slide set forth in claim 1 wherein said diagnostic reagent comprises a reagent for detecting citrate utilization.

18. The test slide set forth in claim 1 wherein said coated film is bonded to said mount by an adhesive at least in the area surrounding said opening.

19. The test slide set forth in any one of claims 1-18 wherein said rear and front walls of said mount each has outer and inner surfaces, a layer of pressure sensitive adhesive on the inner surface of said respective rear and front walls, said coated film being positioned between said walls and having a configuration such that portions of said adhesive layers bond to one another and to said film to secure said plastic film in said mount.

20. The test slide set forth in claim 19 wherein said mount is of a semi-rigid material selected from the group consisting of plastic material and cardboard material.

21. The test slide set forth in claim 20 wherein said rear wall is opaque.

22. The method of making a test slide for performing diagnostic tests for detecting the presence of microorganisms, their enzymes and metabolites, said method comprising providing a plastic film which is dimensionally stable and impervious to liquids, mixing a water soluble carrier and a water soluble diagnostic reagent for a specific microorganism, enzyme or metabolite, said reagent being capable of rehydration such that it changes spectroscopic properties upon exposure to a specific microorganism, enzyme or metabolite, coating said mixture on said film without adhesives between the coating and the film, drying said coated film creating a high melting point, dry and stable, coated film, capable of rehydration at room temperature by application of a microorganism, enzyme or metabolite (with or without the addition of water) to the coating such that its spectroscopic properties change upon exposure to said specific microorganism, enzyme or metabolite, and mounting said coated film in a mount comprising a rear and front wall, said front wall having an opening therein such that a portion of the coated surface of the film is exposed through said opening.

23. The method set forth in claim 22 wherein said step of coating said film comprises applying said mixture to the entire surface of said film.

24. The method set forth in claim 22 wherein said film is selected from the group consisting of polyethylene, PVC (polyvinyl chloride), PET (polyethylene terephthalate), PETG (polyethylene terephthalate glycol modified), polyester, and cellulose triacetate.

25. The method set forth in claim 22 wherein said carrier in said coating is selected from the group consisting of gelatin, polygalacturonic acid, pectin, agar, agarose, cellulose, carboxymethyl cellulose, guar, xanthan, acacia, plant gums, starch, polyvinyl alcohol, polyvinyl chloride and polyacrylamide.

26. The method set forth in claim 22 wherein said diagnostic reagent comprises oxidase.

27. The method set forth in claim 22 wherein said diagnostic reagent comprises a reagent for detecting beta lactamase.

28. The method set forth in claim 22 wherein said diagnostic reagent comprises a reagent for detecting L-aniline amino peptidase.

29. The method set forth in claim 22 wherein said diagnostic reagent comprises a reagent for detecting indole.

30. The method set forth in claim 22 wherein said diagnostic reagent comprises a reagent for detecting catalase.

31. The method set forth in claim 22 wherein said diagnostic reagent comprises a reagent for detecting coagulase.

32. The test slide set forth in claim 22 wherein said diagnostic reagent comprises a reagent for detecting urease.

33. The method set forth inn claim 22 wherein said diagnostic reagent comprises a reagent for detecting $H_2S$.

34. The method set forth in claim 22 wherein said diagnostic reagent comprises a reagent for detecting Voges-Proskauer.

35. The method set forth in claim 22 wherein said diagnostic reagent comprises a reagent for detecting bile esculin.

36. The method set forth in claim 22 wherein said diagnostic reagent comprises a reagent for detecting phosphatase.

37. The method set forth in claim 22 wherein said diagnostic reagent comprises a reagent for detecting B-glucosidase.

38. The method set forth in claim 22 wherein diagnostic reagent comprises a reagent for detecting citrate utilization.

39. The method set forth in claim 22 including the step of providing said coating to said film when the film is in the form of a continuous strip and thereafter severing said strip into separate films.

40. The method set forth in claim 22 wherein said step of providing a mount comprises a mount having rear and front walls, each having outer and inner surfaces, said stop bonding said substrate film too said mount comprises providing a layer of pressure sensitive adhesive on the inner surface of said respective rear and front walls having a configuration such that portions of said adhesive layers bond to one another and to said film to secure said plastic film in said mount.

41. The test slide set forth in claim 22 including the step of forming said mount of a semi-rigid material of plastic material or cardboard material.

42. The method set forth in any of claims 22-41 including the steps of applying a microorganism, its enzyme or metabolite on said coating on said test slide through said opening;

observing any spectroscopic change which occurs indicating said reagent has been changed due to the presence of said microorganism, enzyme or metabolite.

* * * * *